April 25, 1972 G. MURATORE Plant Pat. 3,141
WALNUT TREE
Filed Nov. 21, 1969
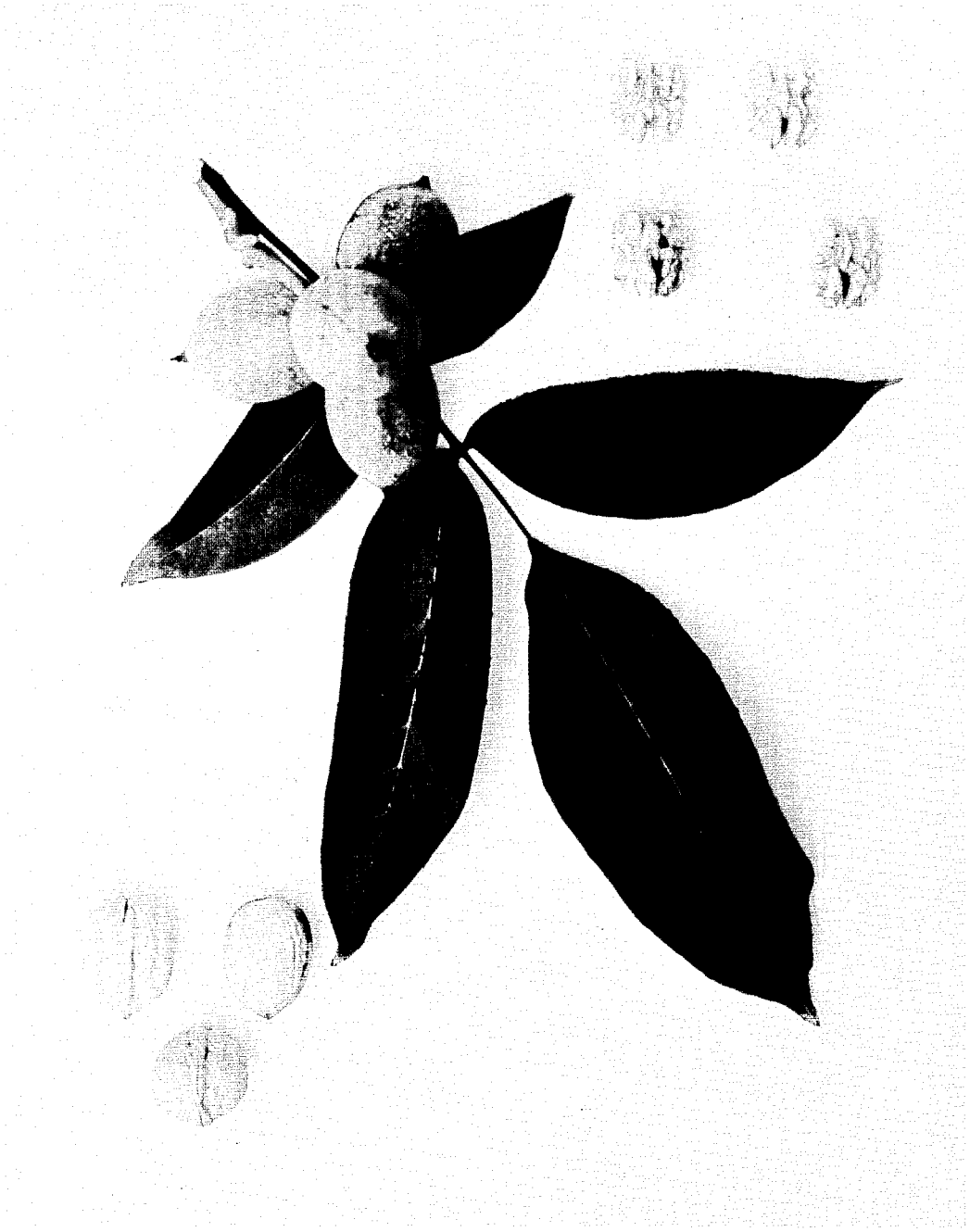
INVENTOR
Giacomo Muratore
BY
Webster & Webster
ATTORNEYS

United States Patent Office

Plant Pat. 3,141
Patented Apr. 25, 1972

3,141
WALNUT TREE

Giacomo Muratore, Merced, Calif., assignor to Guido Bandoni, Merced, Calif.

Filed Nov. 21, 1969, Ser. No. 878,962
Int. Cl. A01h *5/03*
U.S. Cl. Plt.—32 1 Claim

ABSTRACT OF THE DISCLOSURE

A new and distinct variety of English walnut tree which is extremely vigorous and rapid in growth, of large size in maturity, of medium form, of medium density with large to very large leaves, and a regular and heavy to very heavy bearer of large to very large, early maturing nuts borne to a great extent in clusters; many of which clusters are on lateral buds.

ORIGIN OF THE VARIETY

The herein claimed variety of walnut tree was discovered by me growing in my Eureka (unpatented) walnut orchard located near Merced, Merced County, Calif.; the source of the original tree being unknown to me. Upon initial recognition by me of the apparent distinctive characteristics of such original tree of the present variety, I thereafter continued to carefully observe it over a period of time and to confirm the fact of such distinctive characteristics.

ASEXUAL REPRODUCTION OF THE VARIETY

Subsequent to my discovery of the original tree of the present variety, and confirmation—by continued observation—of its distinctive characteristics, the variety was asexually reproduced, on my behalf, by a qualified person; such reproductions having been produced by grafting scions from the original tree on black walnut trees growing in such person's orchard, also located near Merced, Merced County, Calif. In maturity, all of the asexual reproductions of the variety ran true to the original tree in every respect.

SUMMARY OF THE VARIETY

The present variety of walnut tree is, essentially, distinctively characterized by extremely vigorous and rapid growth, by a large size at maturity, by medium form, by medium density but with large to very large leaves, and by an unusual fruiting habit in that it is a regular and heavy to very heavy bearer of large to very large, early maturing nuts which—to a great extent—occur in clusters, many of which are on lateral buds.

As compared to the Eureka, the greater vigor of growth of the tree of the present variety is readily apparent, as is the importantly distinctive characteristic of the clustering habit of the nuts, with many of the clusters appearing on lateral buds and as tends to occur on the Payne (unpatented).

The present variety of walnut tree is additionally distinctively characterized by an evident resistance to sunburn; such an occurrence having been substantially absent both on the original tree and reproduction thereof.

BRIEF DESCRIPTION OF THE DRAWING

The drawing is an illustration, by photographic reproduction in color, of a leafed twig and cluster of nuts, nuts removed from the hull, and kernels removed from the nuts.

DESCRIPTION OF THE VARIETY

The botanical details of this new and distinct variety of walnut tree—with color definitions (except those in common color terms) referenced to Maerz and Paul Dictionary of Color—are as follows:

Tree:

*Parentage.*—Unknown.
*Size at maturity.*—Large.
*Growing habit.*—Extremely vigorous, rapid.
*Form of growth.*—Medium.
*Wood.*—Trunk—light colored bark.
*Production.*—Regular.
*Bearing.*—Heavy to very heavy.
*Foliage.*—Medium dense.
*Time of Leafing (date when tip buds average 1" in length).*—Early. About with Eureka.

Leaves:

*Size.*—Large to very large, average length of leaflets—9½"; average width of leaflets—3½".
*Margin.*—Crenate.
*Petiole.*—Short.
*Glands.*—None.
*Color.*—Top side—Medium green (23–L–9). Under side—Lighter green (22–J–6).

Flowers:

*Flowering habit.*—Slightly before Eureka.
*Age at which tree starts producing catkins.*—Early.
*Number of catkins produced.*—Average.
*Size of catkins.*—Average.
*Time of pollen shedding.*—Early.
*Age at which tree starts producing pistillate flowers.*—Early to very early.
*Number of pistillage flowers produced by young and mature trees.*—Abundant.
*Percentage of lateral buds on long shoots (about 3 feet) of previous season's growth which produce pistillate flowers.*—About 50%.
*Number of pistillate flowers per inflorescence.*—1 to 10.
*Time when pistillate flowers are receptive.*—Early.
*Coincidence of pollen shedding and pistillate receptivity.*—Good.

Nuts:

*Quality.*—Very good.
*Maturity.*—Early, approximately with Payne.
*Evenness of maturity (period between time first and last nuts are ready to harvest).*—Short.
*Tenacity.*—Easy to harvest.
*Cluster.*—Average—2 to 4, sometimes as many as 9.
*Size.*—Large to very large; average length—1¾"; average diameter in suture plane—1¼"; average diameter cheek to cheek—1 9/16".
*Uniformity of size.*—Average.
*Shape.*—Long cylindrical.
*Blossom end.*—Acuminate to beaked; symmetrical.
*Basal end.*—Flat.
*Thickness of shell.*—Medium to thick.
*Seal.*—Well sealed.
*Roughness of shell.*—Smooth.
*Color of shell.*—Light tan (13–D–5).
*Average percentage of kernel to nut.*—51%.

Kernel:

*Size.*—Large.
*Fill.*—Good to very good.
*Kernel plumpness.*—Plump to very plump.
*Amount of kernel shrivel.*—Minimal.
*Speckling of kernels.*—Some speckling.
*Veining.*—Lightly veined (light brown).
*Flavor.*—Very good; without astringency.
*Color.*—Skin—Beige (11–I–5). Somewhat waxy in appearance—Meat—Ivory.

*Resistance to sunburn*: Excellent.
*Resistance to disease and insects*: No unusual susceptibilities noted.

The walnut tree and its nuts herein described may vary in slight detail due to climatic and soil conditions under which the variety may be grown; the present description being of the variety as grown in the Central Valley of California.

I claim:

1. A new and distinct variety of English walnut tree, substantially as illustrated and described, characterzied by extremely vigorous and rapid growth, by large size, by medium form, by medium density but with large to very large leaves, and by the regular and heavy to very heavy bearing of large to very large, early maturing nuts borne to a great extent in clusters, many of which clusters are on lateral buds.

No references cited.

ROBERT E. BAGWILL, Primary Examiner